United States Patent [19]

McChesney et al.

[11] Patent Number: 4,920,147
[45] Date of Patent: Apr. 24, 1990

[54] DEOXOARTEMISININ: NEW COMPOUND AND COMPOSITION FOR THE TREATMENT OF MALARIA

[76] Inventors: James D. McChesney, Rte. 1, Box 340, Etta, Miss. 38627; Mankil Jung, 81 Jeff St., Oxford, Miss. 38655

[21] Appl. No.: 329,669

[22] Filed: Mar. 28, 1989

[51] Int. Cl.$^5$ .................. A61K 31/335; C07D 321/02
[52] U.S. Cl. .................................... 514/450; 549/348
[58] Field of Search ................. 549/358, 348; 514/450

[56] References Cited

PUBLICATIONS

The Merck Index, 10th edition, Publ. Merck & Co., Rayway, N.J., U.S.A., p. APP-3, (1983).

*Primary Examiner*—Nicky Chan
*Attorney, Agent, or Firm*—William D. Stokes

[57] ABSTRACT

This invention provides a new antimalarial compound, deoxoartemisinin, having the formula:

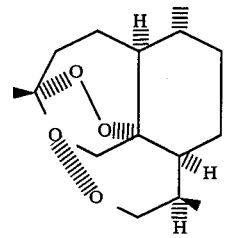

Antimalarial compositions consisting essentially of the compound in admixture with a non-toxic, pharmaceutically-acceptable carrier. A method for treating malaria comprising administering a therapeutically effective concentration of the compound, preferably in admixture with a non-toxic, pharamceutically-acceptable carrier. A method of preparing the doxoartemisinin.

3 Claims, No Drawings

DEOXOARTEMISININ: NEW COMPOUND AND COMPOSITION FOR THE TREATMENT OF MALARIA

BACKGROUND OF THE INVENTION

Far from being a tropical disease of the past, with control within reach, malaria is the number one infectious disease in the world today. Notwithstanding that it was believed that malaria was close to becoming eradicated in the 1960's with the use of quinine, chloroquine and DDT, it was not. Rather malaria is an ever growing problem throughout the world. Approximately 200 million people in endemic areas are infected annually. Worldwide, over two million people die each year from malaria. This shocking reality is due in part to the emergence of drug resistant strains of *Plasmodium falciparum*, the most lethal malarial parasite known to date. More specifically, a high percentage of malaria today is caused by chloroquine-resistant *Plasmodium falciparum*.

Artemisinin (Qinghaosu), first isolated by the Chinese from the leaves of *Artemisia annua* in 1972, is known to be a fast acting, safe and effective drug against chloroquine-resistant and sensitive strains of *Plasmodium falciparum*, as well as against cerebral malaria. No side effects, common to many synthetic antimalarials, have been reported by the Chinese during the past six years of clinical use of artemisinin. Unfortunately, one of the disadvantages of artemisinin is that the compound is only sparingly soluble in either water or oils and thus not readily absorbable by the gastrointestinal tract. Another disadvantage of the drug resides in the fact that large doses (3×400 mg/day per patient) of the drug are required for therapeutic efficacy. A more ideal drug with enhanced antimalarial activity and improved physical and bioavailability properties is an urgent need to treat chloroquine-resistant malaria.

SUMMARY OF THE INVENTION

It was unexpectedly discovered that the compound deoxoartemisinin and compositions thereof are extremely effective in the control and treatment of malaria. The compound provides an antimalarial of greatly increased stability and longer half life over artemisinin. In addition, deoxoartemisinin is readily absorbable through the intestinal tract to provide immediate bioavailability through oral and rectal routes of administration, as well as other routes.

The compound deoxoartemisinin, represented by the following formula:

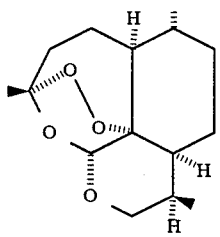

is readily absorbable by the gastrointestinal tract to provide the highest degree of bioavailability of the drug to a malaria patient and is therapeutically effective in smaller dosage units. The invention further comprises compositions consisting essentially of the compound in admixture with a non-toxic, pharmaceutically-acceptable carrier particularly effective in the treatment and control of chloroquine-resistant malaria. In addition, the invention further provides a method of treating and controlling malaria comprising the step of administering a therapeutically effective concentration of the compound, preferably in admixture with a non-toxic, pharmaceutically-acceptable carrier. The invention also provides method of manufacturing the compound of the invention. The dosage unit administered has to be determined by the physical and physiological factors such as body weight, severity of condition, and idiopathy of the patient which factors are readily determined by a medical practitioner in accordance with known techniques.

The structural complexity of artemisinin, particularly the presence of a chemically sensitive lactone ring and peroxide bridge which must be preserved for drug efficacy, has rendered the preparation of derivatives of artemisinin without a carbonyl function heretofore extremely difficult. This invention provides a simple, practical and relatively inexpensive method of removing the C-12 carbonyl group from artemisinin to prepare deoxoartemisinin.

DETAILED DESCRIPTION OF THE INVENTION

The artemisinin used in the preparation of the compound and method of the invention was prepared using the method of Farouk S. ElFeraly and Hala N. ElSohly of The Research Institute of Pharmaceutical Sciences, University of Mississippi, described in a copending application for patent. The method comprises extracting leaves of *Artemisia annua* with hexane, partitioning the hexane extract between hexane and acetonitrile, chromatographing the fraction followed by evaporation and crystallization, a process yielding pure artemisinin which is represented by the following formula:

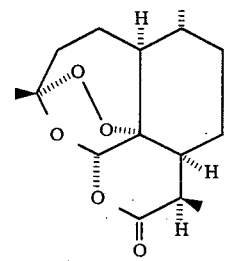

As described in detail in Example I, the method of this invention for preparing the deoxoartemisinin of the invention is essentially a one-step process comprising directly reducing artemisinin with a mild reducing agent followed by refluxing the mixture to yield deoxoartemisinin. Particularly effective as a reducing agent is sodium borohydride with borontrifluoride etherate in dry tetrahydrofuran. Also effective as reducing agents are: (1) lithium borohydrite with borontrifluoride etherate in diethylether, and (2) lithium aluminumhydride with borontrifluoride etherate in diethylether. Utilizing the method of the invention, the biologically essential endoperoxide of the artemisinin is not disturbed.

EXAMPLE I

Under nitrogen atmosphere, 1.0 gram of the artemisinin, was mixed with 13.20 mL of borontrifluoride etherate in dry tetrahydrofuran (20 mL). This solution was added dropwise to an ice-cooled, stirred solution of 0.30 grams of sodium borohydride in dry tetrahydrofuran (20 mL). The solution was stirred while being cooled in the ice bath for 1 hour and subsequently refluxed for 10 minutes. After cooling to 0°, ice (12 mL) was added and the mixture extracted with diethylether (5×30 mL). The extract was dried over magnesium sulfate and concentrated in vacuo to yield a crude product which were purified by flash column chromatography (silica gel) to afford 0.67 gram of homogenous product. Recrystallization from petroleum ether afforded colorless crystals (m.p. 104°–105°). $[\alpha]_D^{18} = +86.25°$ (C 0.4, $CHCl_3$). Anal. Calcd. for $C_{15}H_{24}O_4$; C, 67.16; H, 8.96; O, 23.88. Found: C, 67.34; H, 9.17; O, 23.58. The product, as confirmed by spectral data, was substantially pure deoxoartemisinin, a crystalline, stable compound, soluble in chloroform, diethylether, acetonitrile, cyclohexane and hexane. The compound is lipophilic and was found ideally suited for intramuscular injection in an oily solution.

EXAMPLE II

The intrinsic antimalarial activities of deoxoartemisinin and various control drugs were quantitatively assessed by using modifications of the semiautomated microdilution method of Desjardins. Deoxoartemisinin was dissolved in DMSO and subsequently diluted in culture medium with 10% plasma. Equimolar starting concentrations were predetermined to generate well-defined concentration curves over a 64-fold range of dilutions. Microtiter plates prepared with serial dilutions of drug and parasite suspensions (at 0.5% parasitemia and 1.5% hematocrit) were incubated at 37° C. in an air-tight plexiglass box, which was flushed with 5% oxygen, 5% carbon dioxide, and 90% nitrogen. After 24 hours of incubation, cultures were labeled with tritiated hypoxanthine and incubated for an additional 18–20 hours prior to harvesting particulate matter on fiber glass strips. Hypoxanthine incorporation in each well was determined by scintillation spectrophotometry and served as an index of specific parasite growth rates. Computer-generated concentration-response curves were analyzed by non-linear regression, and 50% inhibitory concentrations were calculated for each drug. The antimalarial tests were conducted using cultures obtained from the Malaria Laboratory, Division of Experimental Therapeutics, WRAIR/WRAMC, Washington, D.C. The W-2 culture utilized in the testing of Example II was of Indochina origin, chloroquine-resistant and mefloquine-sensitive. The other culture D-6, used in the testing of Example II and reported in Table I, is of Sierra Leone origin, chloroquine-sensitive and mefloquine-resistant.

Set out in Table I are the comparative results obtained from in vitro testing the activity of the inventive compound, known antimalarial compounds, artemisinin, and another derivative of artemisinin.

TABLE I

| In Vitro Antimalarial Activity $IC_{50}$ (ng/ml) Clone of *Plasmodium falciparum* | | |
|---|---|---|
| Antimalarial Drug | W-2 | D-6 |
| Chloroquine | 55.66 | 2.69 |
| Mefloquine | 0.74 | 7.30 |
| Pyrimethamine | 39.31 | 0.05 |
| Sulfadoxine | 14332.39 | 16.35 |
| Tetracycline | 10209.47 | 7229.67 |
| Quinine | 59.74 | 10.79 |
| Artemisinin | 1.21 | 2.33 |
| Deoxyartemisinin | — | 761.58 |
| Deoxoartemisinin | 0.15 | 0.58 |

The results of the tests reveal that the compound of the invention, deoxoartemisinin, as compared to artemisinin, exhibited approximately eight times the antimalarial activity in vitro against chloroquine-sensitive malaria and four times the antimalarial activity in vitro against chloroquine-resistant malaria. Nonperoxy metabolites such as deoxyartemisinin, as well as other sesquiterpenes isolated from *Artemisia annua*, which lack a peroxy function, failed to exhibit activity in the antimalarial screening tests as exemplified by the deoxyartemisinin shown in Table I.

We claim:

1. The compound deoxoartemisinin having the formula:

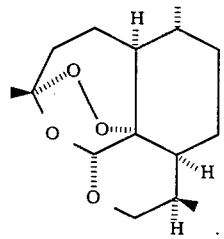

2. The method of treating malaria in mammals comprising administering the compound of claim 1 in a therapeutically effective dosage.

3. A pharmaceutical composition for the treatment of malaria comprising a therapeutically effective amount of the compound of claim 1 in admixture with a non-toxic pharmaceutically acceptable carrier.

* * * * *

UNITED STATES PATENT AND TRADEMARK OFFICE
CERTIFICATE OF CORRECTION

PATENT NO. : 4,920,147

DATED : April 24, 1990

INVENTOR(S) : James D. McChesney

It is certified that error appears in the above-identified patent and that said Letters Patent is hereby corrected as shown below:

The title page should be deleted to appear as per attached title page, to show the correct structural formula in the Abstract.

Signed and Sealed this

Thirtieth Day of July, 1991

Attest:

HARRY F. MANBECK, JR.

*Attesting Officer*  *Commissioner of Patents and Trademarks*

United States Patent

McChesney et al.

Patent Number: 4,920,147
Date of Patent: Apr. 24, 1990

[54] DEOXOARTEMISININ: NEW COMPOUND AND COMPOSITION FOR THE TREATMENT OF MALARIA

[76] Inventors: James D. McChesney, Rte. 1, Box 340, Etta, Miss. 38627; Mankil Jung, 81 Jeff St., Oxford, Miss. 38655

[21] Appl. No.: 329,669

[22] Filed: Mar. 28, 1989

[51] Int. Cl.⁵ .................. A61K 31/335; C07D 321/02
[52] U.S. Cl. .................................... 514/450; 549/348
[58] Field of Search ................. 549/358, 348; 514/450

[56] References Cited
PUBLICATIONS

The Merck Index, 10th edition, Publ. Merck & Co., Rayway, N.J., U.S.A., p. APP-3, (1983).

Primary Examiner—Nicky Chan
Attorney, Agent, or Firm—William D. Stokes

[57] ABSTRACT

This invention provides a new antimalarial compound, deoxoartemisinin, having the formula:

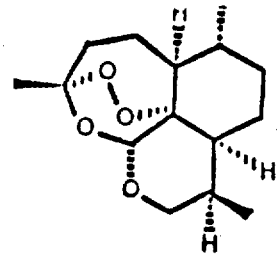

Antimalarial compositions consisting essentially of the compound in admixture with a non-toxic, pharmaceutically-acceptable carrier. A method for treating malaria comprising administering a therapeutically effective concentration of the compound, preferably in admixture with a non-toxic, pharamceutically-acceptable carrier. A method of preparing the doxoartemisinin.

3 Claims, No Drawings